United States Patent [19]

Ackermann

[11] Patent Number: 4,595,362
[45] Date of Patent: Jun. 17, 1986

[54] HANDLE

[75] Inventor: Denis Ackermann, Worben, Switzerland

[73] Assignee: David Mosimann, Switzerland

[21] Appl. No.: 697,588

[22] PCT Filed: May 11, 1984

[86] PCT No.: PCT/CH84/00072
§ 371 Date: Jan. 11, 1985
§ 102(e) Date: Jan. 11, 1985

[87] PCT Pub. No.: WO84/04447
PCT Pub. Date: Nov. 22, 1984

[30] Foreign Application Priority Data

May 11, 1983 [CH] Switzerland .................. 2590/83

[51] Int. Cl.$^4$ .................................. A61C 1/14
[52] U.S. Cl. ............................ 433/129; 433/127; 279/83
[58] Field of Search .................. 433/129, 127, 147; 279/83, 67, 41 R

[56] References Cited

U.S. PATENT DOCUMENTS

| 310,467 | 1/1885 | Ross | 433/129 |
| 610,483 | 9/1898 | Fritz | 433/127 |
| 2,938,698 | 5/1960 | Johnson | 279/83 |
| 4,199,160 | 4/1980 | Bent | 433/127 |

FOREIGN PATENT DOCUMENTS 40692 10/1932 France .................. 433/129

Primary Examiner—John J. Wilson

[57] ABSTRACT

A screw (22) having the circumference of its head (23) toothed like a pinion firmly holds the cylindrical shank of a rotary tool in position in a slotted sleeve (17). A rack (25) on the front end of the hollow cylindrical spindle (24) meshes with the pinion or head (23) of the screw (22). The retraction or advance of the rack (25) is effected by a grooved ring (20) through screws (35,36) whose cylindrical heads are engaged in two helical guide slots provided in a nosepiece (19) and which are anchored in a pusher ring (28) indirectly applied against the rear face of the hollow cylindrical spindle (24).

6 Claims, 5 Drawing Figures

HANDLE

The present invention is directed to a handle, particularly but not exclusively for use in dentistry, made up of a rotor, namely a shaft mounted on at least two antifriction bearing means, with the rear end of the shaft being provided with a connection for any kind of transmission and the opposite end thereof comprising a cylindrical socket wherein an also cylindrical sleeve is fitted in which, at least partly, at least one longitudinal slot is provided thoroughly penetrating the sleeve, said sleeve being intended to receive the cylindrical shank of a round tool of any kind, as well as of a tripartite body forming a shell of the rotor, with the first part thereof comprising an at least partly cylindrical nosepiece in which the rotor is suspended through its antifriction bearing means, the second part comprising a grooved ring embracing with sliding friction the cylindrical portion of the nosepiece, and the third part comprising a rear member which is secured to the rear portion of the nosepiece.

In handles of this kind used at the present time particularly in dentistry, a known problem is the difficulty of retaining in the sleeve the cylindrical shank of any round tool. In fact, the problem is to ensure a firm hold of two cylindrical elements which are non-slidably fitted together, and intended to be driven by the same rotary drive and of which one, the tool, is in addition to be subjected at the end of its shank to a frictional force. In other words, the cylindrical shank of a frictional force. In other words, the cylindrical shank of a rotary tool fitted with non-sliding friction in an also cylindrical sleeve is to be fixed in this sleeve in a way such that if a strong axial torque is imparted to the sleeve and the tool (grinding disc, milling cutter) has to overcome a frictional force, the cylindrical shank will not slip in the sleeve.

Handles employed in dentistry may, quite generally, be classified in two groups, depending on their purpose or use: a first group including handles for practicing dentists and having a tool shank receiving caliber varying between 1.60 and 2.35 mm, and a second group including laboratories' handles having the same calibers varying between 2.35 and 3.17 mm. Nevertheless, irrespective of their destination or use, these handles have basically the same technical properties relating to the manner of holding fast a cylindrical shank-type tool. They are all provided with a cylindrical sleeve in which the shank of the tool is received with a non-sliding fit and which has at least one longitudinal slot penetrating through the sleeve along at least a part of the extension thereof. Two, or even four, such slots may be provided, depending on the design. To fix and hold the cylindrical tool shank in the sleeve, the flexibility due to the above mentioned properties thereof is utilized. If the sleeve itself is also cylindrical, the tool shank holding force is to be exerted perpendicularly to the axis thereof, which may be embodied by a cam, a lever, by an kind of spring or spring washers, or even by balls or rollers acting on any member of complementary shape. If the sleeve is conically tapered or of a combined cylindrical and conical shape, the force for holding the tool shank may also be exerted perpendicularly to the axis thereof by means such as just mentioned, however, in most instances, it will be exerted lengthwise by means of a tightening member, with the conical portion of the sleeve being compressed by a part of complementary shape.

Prior art means for holding the tool shank fast in the sleeve, as provided particularly in dentistry handles, have proved not quite effective, i.e., since mainly laboratories' handles were concerned which are used for rough trimming, thus exposed to considerable frictional forces, it was observed that the tool shank had the tendency of advancing or of slipping in the sleeve.

The invention intends to eliminate these drawbacks while still preserving simplicity in manipulation of the handle.

This is achieved by the features set forth in the claims.

The accompanying drawings show by way of example one embodiment of the invention.

Figure 1:
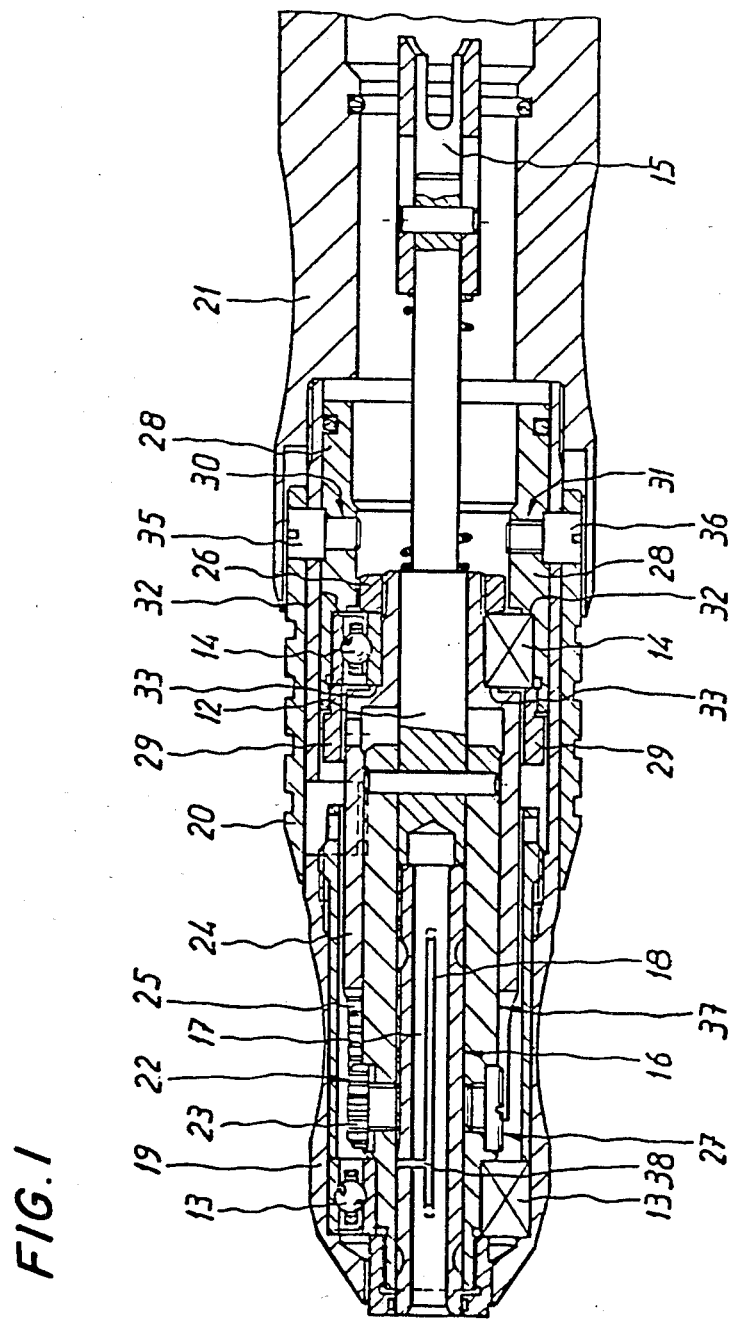
FIG. 1 is a sectional view of the handle in accordance with the invention.

The handle is intended for retaining the cylindrical shank 11 of a round tool of any kind (grinding disc, milling cutter). To this end, it comprises a rotor, namely a shaft 12 which is mounted by means of at least two antifriction bearing means 13, 14. The rear end of shaft 12 is provided with a connection for a transmission 15 permitting to couple the rotor to a supply means, while the opposite end of the shaft comprises a cylindrical socket 16 in which a correspondingly shaped sleeve 17 is fitted. A through-going partial, lengthwise extending double slot 18 is provided in sleeve 17. The rotor is enclosed in a shell formed by a body assembled of three parts, a partly cylindrical nosepiece 19 in which the rotor is actually suspended by means of its antifriction bearing means 13, 14, a grooved ring 20 embracing with sliding friction the cylindrical portion of nosepiece 19, and a rear member 21 which is secured to the rear portion of nosepiece 19.

The retention of the cylindrical shank 11 of the tool in sleeve 17 is secured by a screw 22 having a head 23 which is serrated along its circumference like a pinion. The threaded shank of the screw 22 is screwed into a corresponding taphole extending in rotor shaft 12, perpendicularly thereto, until it butts and applies against one of the sections of sleeve 17 formed by the double slot 18 thereof.

It will be understood that the lengthwise double slot 18 makes sleeve 17 flexible to a certain extent. By butting and applying the base of the shank of screw 22 against one of the sections of sleeve 17 formed by the double slot 18, this flexibility is utilized to secure the cylindrical tool shank 11 in place in sleeve 17. The sleeve is most flexible in the middle of the oblong space formed by double slot 18. Therefore, it is convenient to make the base of the shank of screw 22 apply substantially at this location.

In a more elaborate embodiment, sleeve 17 is provided in addition with a transverse slot 38 which extends through the sleeve from one side to the other and intersects with the double slot 18. One of the sectins formed by the double slot 18 of sleeve 17 is thereby transformed into a kind of a flexible blade. By butting and applying the base of shank of screw 22 against the front end of the blade, the force holding the cylindrical tool shank 11 in place in sleeve 17 is further augmented.

To actuate screw 22, a hollow cylindrical spindle 24 is provided embracing at least partly rotor shaft 12 and carrying a rack 25 on its front end. Rack 25 meshes with the pinion formed by the circumference of head 23 of screw 22. Hollow cylindrical spindle 24 extends between rotor shaft 12 and the inner race of rear bearing means 14 to which it is secured by a nut 26. This means that hollow cylindrical spindle 24 follows the rotary motion of rotor shaft 12. However, longitudinally, the spindle remains independent of the rotor shaft, to permit the operation of rack 25. At this point of description, the part lengthwise movable relative to rotor shaft 12 consists of the hollow cylindrical spindle 24, the rear bearing means 14, and the nut 26.

To ensure guidance of rack 25, namely to prevent it so to speak from derailment, a recess 37 is provided in the front end portion of hollow cylindrical spindle 24, opposite to rack 25, intended to be engaged by a guide screw 27. The diameter of the head of guide screw 27 is equal to the width of said recess 37, while the shank of the screw is fixed in rotor shaft 12.

The inventive handle must further be provided with a means for effecting the retraction and extension, in the lengthwise direction of the rotor shaft, of rack 25, i.e. the tightening or loosening, respectively, of screw 22. The main component part thereof is a pusher ring 28 mounted between the inner wall of nosepiece 19 and the outer race of rear bearing means 14 to which it is secured by a nut 29 in a manner such that the base of the nut comes to apply against the front face of the outer race of rear bearing means 14. Two tapholes 30, 31 are provided at opposite locations in the outer wall of pusher ring 28. The rim 32 comes to apply against the rear face of the outer race of rear bearing means 14 which, in turn, applies by the front face of its inner race against a shoulder 33 provided for this purpose on hollow cylindrical spindle 24. In the cylindrical portion of nosepiece 19, two right hand helical slots are provided at opposite sides, of which one 34 is partly shown in FIGS. 2 and 4. By bringing the two opposite tapholes 31 provided in the external wall of the pusher ring 28 to coincidence with the two opposite helical slots provided in the cylindrical portion of nosepiece 19, then introducing into said holes 30, 31 two screws 35, 36 having cylindrical heads which are used to form sliding guide blocks within said slots, and, finally, having the cylindrical heads of screws 35, 36 extended up to corresponding recesses which are provided in the grooved ring 20 embracing with sliding friction the cylindrical portion of nosepiece 19, the above mentioned means for effecting the retraction and extension is perfected.

Figure 2:
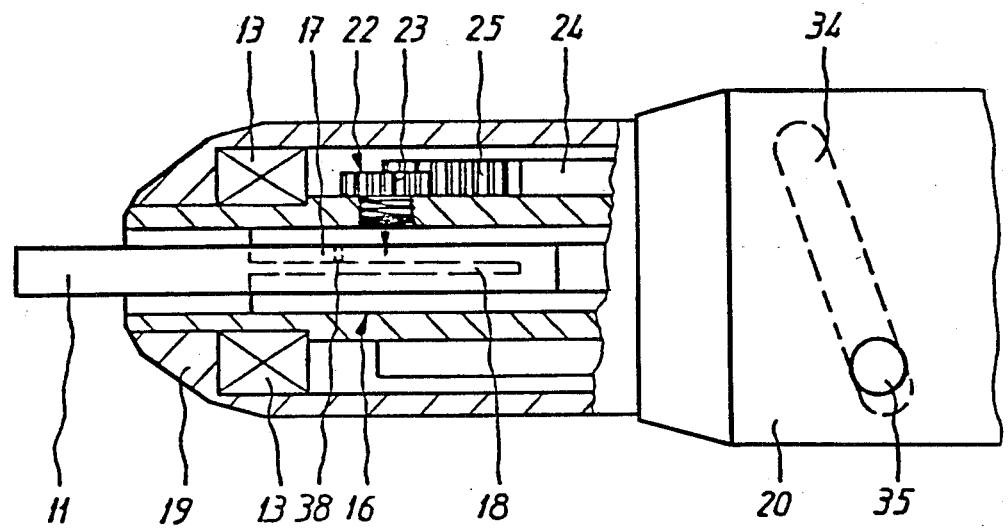
FIGS. 2 and 4 are partial diagrammatical sectional views of the nosepiece of a handle such as shown in FIG. 1.
Figure 3:
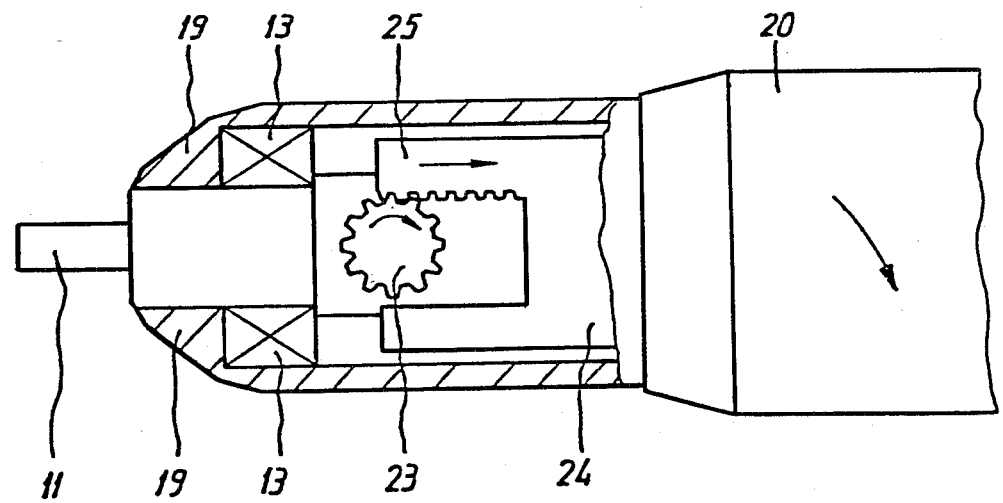
FIG. 3 is a top plan view corresponding to FIG. 2.
Figure 4:
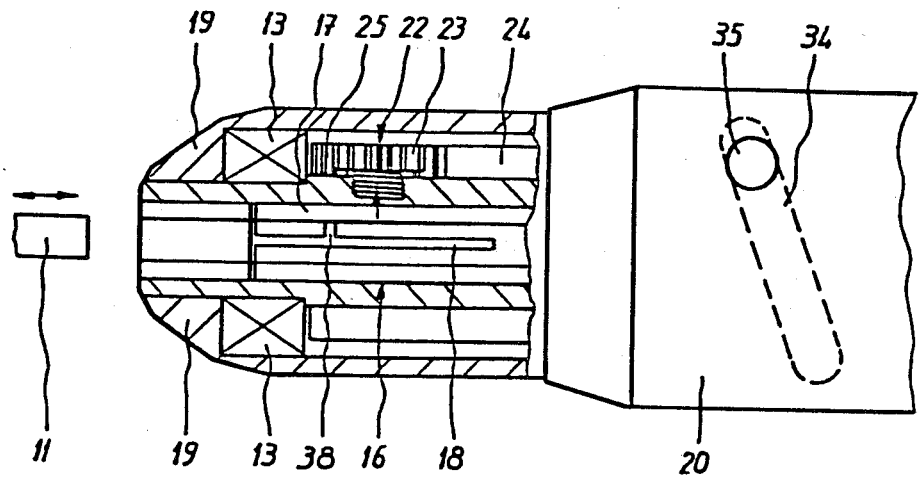
Figure 5:
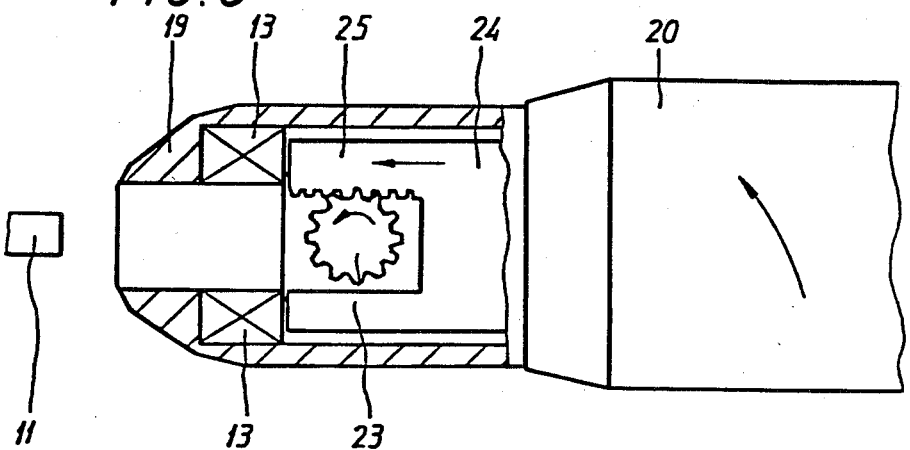
FIG. 5 is a top plan view corresponding to FIG. 4.

FIGS. 2 and 3 are partial diagrammatical showings of the handle in the position with screw 22 tightened, while FIGS. 4 and 5 show the same handle with screw 22 loosened.

The handle part lengthwise movable relative to rotor shaft 12 was described above as comprising hollow cylindrical spindle 24, rear bearing means 14, and nut 26. This sub-assembly must now be completed with pusher ring 28 and nut 29 securing pusher ring 28 to the outer race of rear bearing means 14, as well as with groove ring 20 which in turn is secured to pusher ring 28 by the cylindrical heads of screws 35, 36.

Upon actuating grooved ring 20 by turning it to the left, rack 25 is retracted, thus screw 22 is tightened, as shown in FIGS. 2 and 3.

Upon actuating grooved ring 20 by turning it to the right, rack 25 is advanced, thus screw 22 is loosened.

To ensure a satisfactory function, sufficient spaces must be provided for the lengthwise movement of the mobile part of the handle relative to rotor shaft 12.

In the embodiment of the invention described above, the range of tightening and loosening, i.e. the angle of extension of the helical slots in the cylindrical portion of nosepiece 19, is substantially equal to 20°, which causes a travel of the screw 22 of about 7 to 10/100 mm.

Tests made with the inventive handle have proved that the firm hold of a tool shank 11 in sleeve 17 is ensured to a maximum. In addition, in tightened position, the bearing means 13, 14 of the rotor remain free from any stress. Also, sleeve 17 can easily be exchanged. This means that a sleeve adapted to the caliber of the tool shank 11 to be clamped can be employed. The inventive handle is simple to manipulate and does not require any special tools, neither in practice nor in maintenance. Finally, even though the handle is particularly intended for dentistry, it may equally well be employed in other technical fields, for example, in surgery, micromechanics, in jewelry, or by goldsmiths.

I claim:

1. A handle comprising: a rotor shaft (12) mounted on at least two antifriction bearing means (13, 14), with a rear end of the shaft (12) being provided with a connection for a transmission (15), and an opposite end of the shaft comprising a cylindrical socket ((16); a cylindrical sleeve (17) fitted in the socket and having at least one longitudinal slot (18) penetrating the sleeve, the sleeve (17) being adapted to receive a cylindrical shank (11) of a tool; a tripartite body forming a shell for the rotor shaft, with a first part thereof comprising an at least partly cylindrical nosepiece (19) in which the rotor shaft is suspended through the antifriction bearing means (13, 14), a second part comprising a grooved ring (20) embracing with sliding friction a cylindrical portion of the nosepiece (19), and a third part comprising a rear member (21) which is secured to a rear portion of the nosepiece (19); at least one screw means (22) having a circumferentially toothed upper portion (23) forming a pinion and having a threaded portion seated in the rotor shaft (12) and extending perpendicularly to the shaft, the screw means being rotatable to locally compress the sleeve (17); a hollow cylindrical spindle (24) at least partly surrounding the rotor shaft (12) and extending between the shaft and an inner race of a rear one of the bearing means (14) to which the spindle is joined in a manner so as to follow rotary motion of the rotor shaft (12) yet remain axially independent of the shaft, the spindle having a front end with a rack (25) engaged with the pinion (23) for rotation of the screw means (22) with axial motion of the spindle with respect to the shaft, to compress and release the sleeve (17).

2. A handle according to claim 1, characterized the front end of the hollow cylindrical spindle is provided, opposite to the rack (25), with a recess (37) which, in order to guide the rack (25), is engaged by a guide element (27) fixed in the rotor shaft (12).

3. A handle comprising: a rotor shaft (12) mounted on at least two antifriction bearing means (13, 14), with a rear end of the shaft (12) being provided with a connection for a transmission (15), and an opposite end of the shaft comprising a cylindrical socket (16); a cylindrical sleeve (17) fitted in the socket and having at least one longitudinal slot (18) penetrating the sleeve, the sleeve (17) being adapted to receive a cylindrical shank (11) of a tool; a tripartite body forming a shell for the rotor shaft, with a first part thereof comprising an at least partly cylindrical nosepiece (19) in which the rotor shaft is suspended through the antifriction bearing means (13, 14), a second part comprising a grooved ring

(20) embracing with sliding friction a cylindrical portion of the nosepiece (19), and a third part comprising a rear member (21) which is secured to a rear portion of the nosepiece (19); at least one screw means (22) having a circumferentially toothed upper portion (23) forming a pinion and having a threaded portion seated in the rotor shaft (12) and extending perpendicularly to the shaft, the screw means being rotatable to locally compresa the sleeve (17); a hollow cylindrical spindle (24) at least partly surrounding the rotor shaft (12) and extending between the shaft and an inner race of a rear one of the bearing means (14) to which the spindle is joined in a manner so as to follow rotary motion of the rotor shaft (12) yet remain axially independent of the shaft, the spindle having a front end with a rack (25) engaged with a pinion (23) for rotation of the screw means (22) with axial motion of the spindle with respect to the shaft, to compress and release the sleeve (17); the sleeve (17) having a partial transverse slot (38) which thoroughly penetrates the sleeve and intersects with the longitudinal slot (18) so as to form a blade to be compressed by the screw means (22).

4. A handle according to claim 3, wherein the front end of the hollow cylindrical spindle (24) is provided, opposite to the rack (25), with a recess (37) which, in order to guide the rack (25), is engaged by a guide element (27) fixed in the rotor shaft (12).

5. A handle according to any of claims 1, 2, 3 or 4, including, a pusher ring (28) having two opposite tapped holes (30, 31) in its outer wall, mounted between an inner wall of the nosepiece and an outer race of the rear bearing means (H) to which it is firmly joined, the nosepiece (19) provided in its cylindrical portion with two opposite helical guide slots (34) in a manner such that the two opposite tapholes (30, 31) of the outer wall of the pusher ring (28) coincide with the opposite helical slots (34) of the cylindrical portion of the nosepiece (19), and two screws (35, 36) having cylindrical heads and connected in said tapholes (30, 31), with their cylindrical heads serving as guide elements sliding in said helical slots (34).

6. A handle according to claim 5, wherein the cylindrical heads of the screws (35,36) extend up to corresponding recesses provided in the grooved ring (20) which is engaged with sliding friction the cylindrical portion of the nosepiece (19).

* * * * *